US00PP33222P2

(12) United States Plant Patent
Romme

(10) Patent No.: US PP33,222 P2
(45) Date of Patent: Jun. 29, 2021

(54) ***LAVANDULA* PLANT NAMED 'TWIN SUMMER'**

(50) Latin Name: *Lavandula stoechas*
Varietal Denomination: TWIN SUMMER

(71) Applicant: BG Breeding ApS, Odense (DK)

(72) Inventor: Henrik Agerskov Romme, Gudberg (DK)

(73) Assignee: BG Breeding APS

( * ) Notice: Subject to any disclaimer, the term of this patent is extended or adjusted under 35 U.S.C. 154(b) by 0 days.

(21) Appl. No.: 16/932,033

(22) Filed: Jul. 17, 2020

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 5/02
See application file for complete search history.

(56) References Cited

U.S. PATENT DOCUMENTS

PP20,840 P2 * 3/2010 Larkman ..... A01H 5/02
Plt./445

* cited by examiner

*Primary Examiner* — Kent L Bell
(74) *Attorney, Agent, or Firm* — Cassandra Bright

(57) ABSTRACT

A new and distinct *Lavandula* cultivar named 'TWIN SUMMER' is disclosed, characterized by large sterile terminal bracts uniquely colored violet with irregular white spots and stripes. Individual flower corolla color is dark violet. Plants are typically upright in growth habit, and begin flowering very early. The new variety is a *Lavandula*, normally produced as an outdoor garden or container plant.

2 Drawing Sheets

Figure 1:
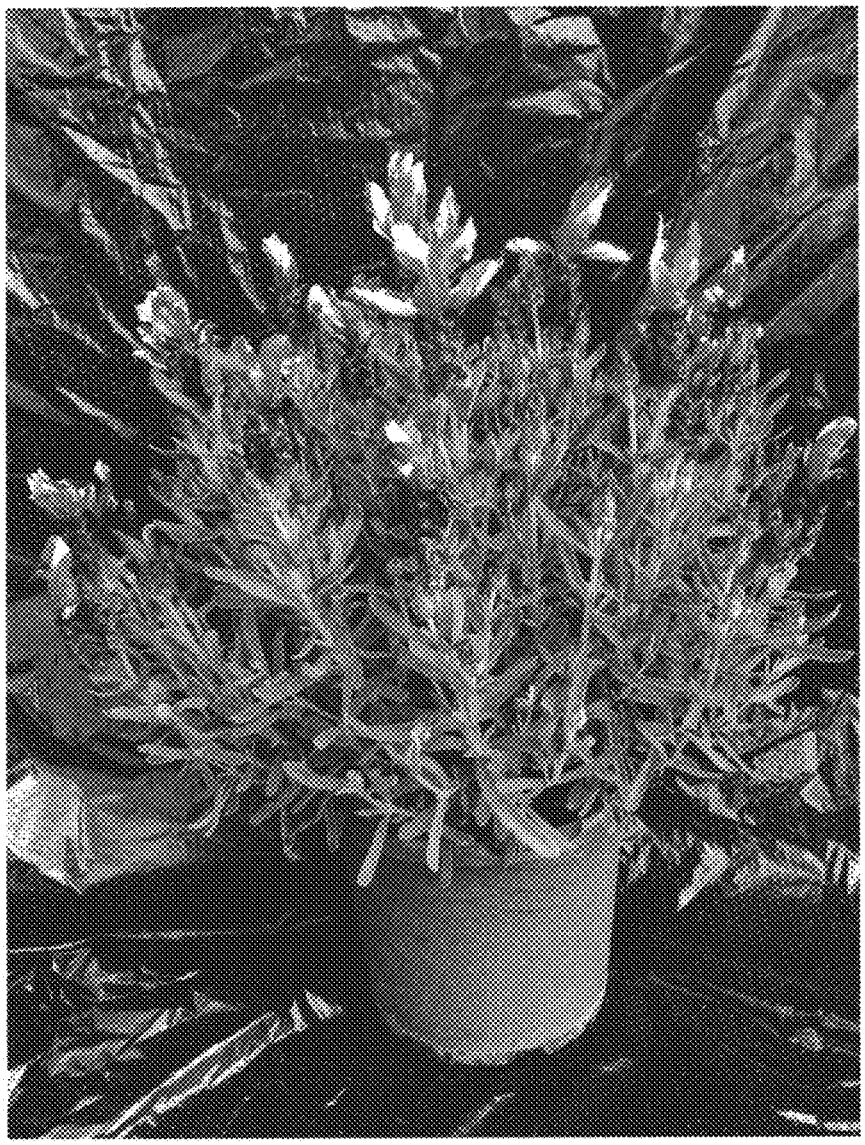

Latin name of the genus and species: *Lavandula stoechas*.
Variety denomination: 'TWIN SUMMER'.

BACKGROUND OF THE INVENTION

The new *Lavandula* cultivar is a product of a planned breeding program conducted by the inventor in Odense, Denmark. The objective of the breeding program was to produce new *Lavandula stoechas* varieties for ornamental commercial applications. The cross resulting in this new variety was made during July of 2016.

The seed parent is the, unpatented variety referred to as *Lavender* '6612A'. The pollen parent is the unpatented variety 'Giant Summer'. The new variety was selected Jul. 28, 2017 by the inventor in a group of seedlings resulting from the 2016 crossing, in a research greenhouse in Odense, Denmark.

Asexual reproduction of the new cultivar was performed by vegetative terminal cuttings. This was first performed at a research greenhouse in Odense, Denmark during July of 2017 and has shown that the unique features of this cultivar are stable and reproduced true to type in at least 6 successive generations. Date of first sale was Jun. 13, 2020, occurring in Denmark. This sale was made directly by the inventor or one who obtained the claimed invention directly or indirectly from the inventor. This sale and all public disclosures made between Jun. 13, 2020 and the filing of this application fall within the exception allowed under 102(b)(1).

SUMMARY OF THE INVENTION

The cultivar 'TWIN SUMMER' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TWIN SUMMER' These characteristics in combination distinguish 'TWIN SUMMER' as a new and distinct *Lavender* cultivar:

1. Sterile terminal bracts are Violet with irregular white spots/stripes.
2. Corolla of individual flowers are dark violet.
3. Large infertile bracts.
4. Upright plant growth.
5. Very early flowering.

PARENT COMPARISON

Plants of the new cultivar 'TWIN SUMMER' are similar to plants of the seed parent, in most horticultural characteristics, however, plants of the new cultivar 'TWIN SUMMER' produce terminal sterile bracts which are violet with irregular white spots and stripes, sterile bracts of the seed parent are solid violet. Additionally, sterile terminal bracts of the new variety are larger than those of the seed parent.

Plants of the new cultivar 'TWIN SUMMER' are similar to plants of the pollen parent in most horticultural characteristics, however, plants of the new cultivar 'TWIN SUMMER' produce terminal sterile bracts which are violet with irregular white spots and stripes, sterile bracts of the pollen parent are solid violet. Additionally, plants of the new variety begin flowering earlier than those of the pollen parent.

COMMERCIAL COMPARISON

Plants of the new cultivar 'TWIN SUMMER' are comparable to the variety *Lavandula* 'Larkman Bee', U.S. Plant Pat. No. 20,840. The two *Lavandula* varieties are similar in most horticultural characteristics, however, the new variety 'Twin Summer' differs in the following:

1. The new variety 'TWIN SUMMER' produces longer terminal sterile bracts.
2. Sterile terminal bracts of the new variety are violet with irregular white spots and stripes, sterile terminal bracts of 'Larkman Bee' are solid purple.

Plants of the new cultivar 'TWIN SUMMER' can also be compared to the commercial variety *Lavandula* 'White Giant Summer' (unpatented). These varieties are similar in most horticultural characteristics however, the new variety 'TWIN SUMMER' differs in the following:

1. Terminal sterile bracts of 'TWIN SUMMER' are violet with irregular white spots and stripes, sterile bracts of 'White Summer Giant' are solid white.
2. The corolla color of 'Twin Summer' is darker violet than the corolla of 'White Summer Giant'.
3. Plants of 'TWIN SUMMER' begin flowering earlier than this comparator.

BRIEF DESCRIPTION OF THE PHOTOGRAPHS

The accompanying photograph in FIG. 1 illustrates in full color a typical plant of 'TWIN SUMMER' grown outdoors in Odense, Denmark. The plant grown in a commercial 1 gallon container. Age of the plants photographed is approximately 30 weeks from a rooted cutting.

Figure 2:
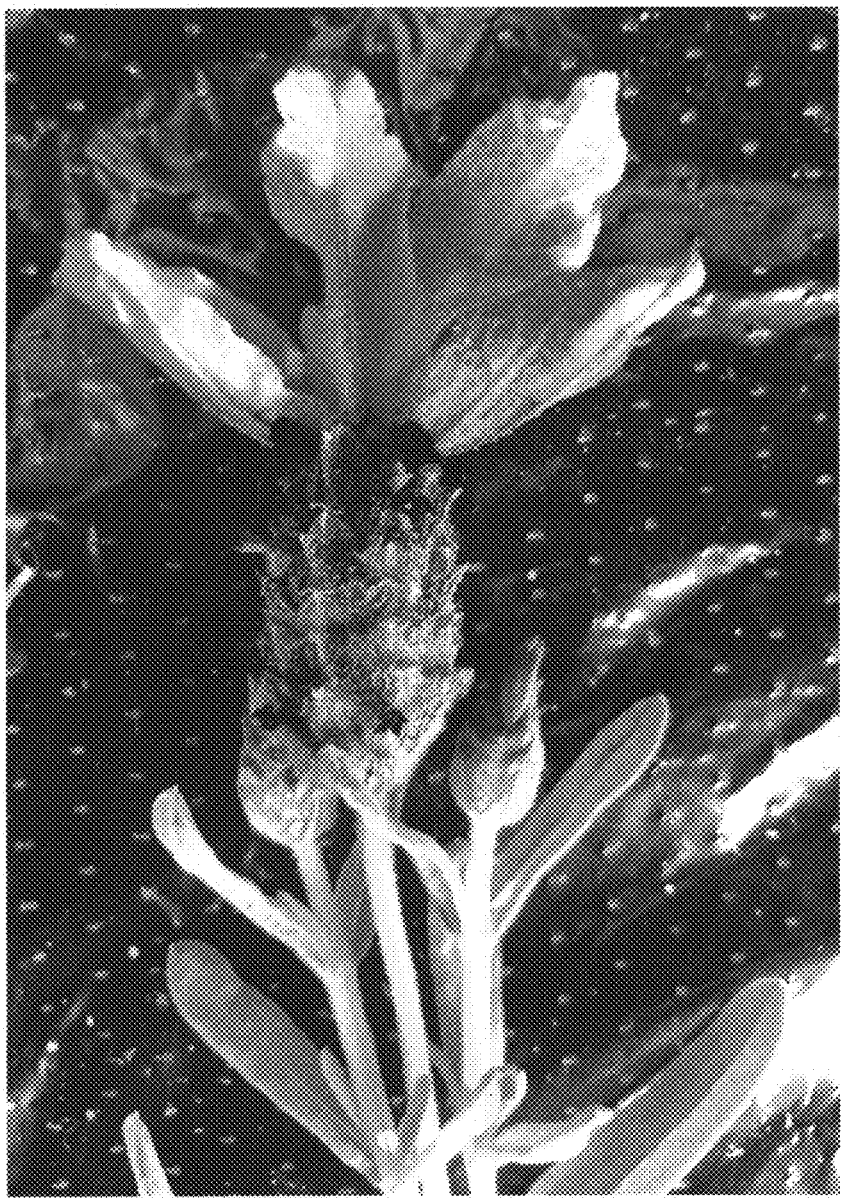

FIG. 2 illustrates a close up of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'TWIN SUMMER' plants which were grown in Odense, Denmark. Unrooted cuttings were stuck in a heated greenhouse during week 5 of 2020. Plants were pinched 3 times, then potted into 2 liter pots during week 15 and grown in an unheated greenhouse. Plants were placed outdoors week 20. The growing temperature ranged from 8° C. to 25° C. during the day and from 1° C. to 15° C. during the night. Measurements and numerical values represent averages of typical plant types. The description was made in June of 2020.

Botanical classification: *Lavandula stoechas* 'TWIN SUMMER'.

PROPAGATION

Time to initiate roots: About 13 days at approximately 18° C.

Time to produce a rooted cutting: About 18 days at 18° C.

PLANT

Age of plant described: Approximately 17 weeks from a rooted cutting.

Pot size: 2 liter.

Plant habit: Upright.

Plant spread: Approximately 28 cm.

Plant height: Approximately 30 cm.

Growth rate: Approximately 3.5 mm/day after potting.

Length of primary lateral branches: Approximately 25 cm.

Diameter of lateral branches: Approximately 0.4 cm.

Quantity of lateral branches: About 24.

Branches:

*Color*.—Near RHS 144B.

*Texture/pubescence*.—Pubescent — Stellate.

Internode length: Approximately 2.5 cm.

Root description: Fine, well branched, becoming woody with age. Brown to tan, not accurately measured with The R.H.S. Colour Chart.

FOLIAGE

Leaf:

*Arrangement*.—Opposite.

*Quantity*.—Approximately 9 leaf pairs per main branch.

*Average length*.—Approximately 4.5 cm.

*Average width*.—Approximately 0.9 cm.

*Shape of blade*.—Lorate.

*Apex*.—Obtuse.

*Base*.—Acute.

*Attachment*.—Sessile.

*Margin*.—Entire.

*Texture of top surface*.—Softly pubescent.

*Texture of bottom surface*.—Softly pubescent.

*Color*.—Young foliage upper side: Near RHS 137A. Young foliage under side: Near RHS 137D. Mature foliage upper side: Near RHS 137C. Mature foliage under side: Near RHS 137D.

*Venation*.—Type: Reticulate. Venation color upper side: Near RHS 137A. Venation color under side: Near RHS 137D.

*Petiole*.—Absent.

FLOWER

Bloom period: June-September. (approximately 9 weeks from potting).

Inflorescence:

*Form*.—Small single flower in verticillasters arranged in spikes with large showy terminal bracts.

*Quantity of rows of flowers per verticillaster*.—8-9.

Individual flowers:

*Arrangement*.—Corolla tube is 2-lipped. Upper lip 2 lobes. Lower lip 3 lobes. Size individual flowers: Length: Approximately 0.8 cm. Diameter: Approximately 0.5 cm.

*Upper lip*.—Apex: Obtuse. Margin: Entire. Texture: Glabrous.

*Lower lip*.—Apex: Acute to mucronate. Margin: Entire. Texture: Glabrous.

*Throat*.—Diameter: 2 mm. Color: Violet-Blue N92A. Texture: Glabrous.

*Tube*.—Length: 4 mm. Diameter: 2 mm. Texture: Glabrous. Color: Violet-Blue 90A.

*Inflorescence size, excluding terminal bracts*.—Length: Approximately 2.5 cm. Width: Approximately 1.5 cm. Coloration of individual flowers and entire spikes, excluding terminal bracts: Immature: Near RHS Violet-Blue N92B. Mature: Near RHS Violet-Blue N92B. Fading: Near RHS Violet-Blue N92B.

*Lastingness*.—Inflorescence about 4 weeks, individual flowers about 2 to 3 weeks.

Terminal bracts:
*Quantity.*—4.
*Length.*—Approximately 3.5 cm.
*Width.*—Approximately 1.5 cm.
*Aspect.*—Slightly Undulating.
*Duration on plant.*—Approximately 1.5 weeks, with good color. Persistent.
*Shape.*—Oblong.
*Apex.*—Obtuse to broad acute.
*Margin.*—Entire, somewhat undulate.
*Base.*—Truncate.
*Texture.*—Glabrous.
*Color.*—Upper side of immature bract: Near RHS Violet 86C with spots/stripes near White 155B. Under side of immature bract: Near RHS Violet 86C with spots/stripes near White 155B. Upper side of mature bract: Near RHS Violet 86C with spots/stripes near White 155B. Under side of mature bract: Near RHS Violet 86C with spots/stripes near White 155B.

Flower bud:
*Shape.*—Oblong.
*Length.*—3 mm.
*Width.*—2 mm.
*Texture.*—Pubescent.
*Color.*—RHS Violet-Blue N92D.

Sepals:
*Description.*—5 fused into a tubular calyx about 5 mm long and 3 mm wide.
*Apex.*—Acute.
*Margin.*—Entire.
*Texture.*—Roughly pubescent exterior, interior softly pubescent.
*Exterior color.*—RHS Violet 86D, base near Yellow-Green 145C.
*Interior color.*—RHS Greyed-Purple N187B.

Fragrance: Not detected in the flower specifically, but the plant has the typical lavender fragrance.

Peduncle:
*Peduncle length.*—Approximately 4 cm.
*Peduncle diameter.*—Approximately 0.2 cm.
*Aspect.*—Upright.
*Color.*—Near RHS Yellow-Green 144B.
*Texture.*—Softly pubescent.

REPRODUCTIVE ORGANS

Androecium:
*Stamens.*—4.
*Filament length.*—Approximately 0.6 cm incl. the 0.5 cm part that is fused with corolla.
*Anther shape.*—Capitate.
*Anther length.*—Approximately 0.7 mm.
*Anther color.*—Near RHS Yellow-Orange 14A.
*Pollen quantity.*—Moderate, colored near Yellow-Orange 14A.

Pistil:
*Number.*—1.
*Length.*—Approximately 0.6 cm.
*Style.*—Length: Approximately 0.5 cm. Color: Near RHS Yellow 11D.
*Stigma.*—Shape: Capitate. Color: Near RHS Blue 103A. Ovary: Less than 1 mm, colored near Yellow-Green 145A.

OTHER CHARACTERISTICS

Disease/pest resistance: Neither resistance nor susceptibility to the normal diseases and pests of *Lavandula stoechas*. has been observed. *Lavandula* is not affected by many diseases and pests. However, *Botrytis* and some root rot pathogens can be disease problems, especially in overly wet conditions. Various species of White Fly may infect *Lavandula.*

Drought tolerance and cold tolerance: Tolerates high temperature to at least 32° C. Tolerates low temperatures to approximately −2° C. While specific drought tolerance has not been observed, once plants are established very little water is necessary to maintain plants.

Fruit/seed production: Fruit and seed production not observed.

What is claimed is:

1. A new and distinct cultivar of *Lavandula* plant named 'TWIN SUMMER' as herein illustrated and described.

* * * * *